United States Patent
Mehlberg et al.

[11] Patent Number: 5,849,965
[45] Date of Patent: Dec. 15, 1998

[54] MULTISTAGE ALKYLATION PROCESS

[75] Inventors: Robert L. Mehlberg, Wheaton; George A. Huff, Jr., Naperville, both of Ill.

[73] Assignee: Amoco Corporation, Chicago, Ill.

[21] Appl. No.: 861,475

[22] Filed: May 22, 1997

[51] Int. Cl.⁶ .............................. C07C 2/70; C07C 2/66; C07C 2/62; C07C 2/00
[52] U.S. Cl. ......................... 585/323; 585/323; 585/313; 585/332; 585/449; 585/458; 585/462; 585/714; 585/716; 585/730; 585/731
[58] Field of Search ................................. 585/312, 313, 585/323, 331, 447, 458, 462, 714, 716, 730, 731

[56] References Cited

U.S. PATENT DOCUMENTS

| | | | |
|---|---|---|---|
| 2,476,750 | 7/1949 | Matuszak | 260/683.4 |
| 2,582,047 | 1/1952 | Lee | 260/671 |
| 2,989,574 | 6/1961 | Pfefferle et al. | 260/683.44 |
| 3,560,587 | 2/1971 | Borst, Jr. | 260/683.48 |
| 3,678,120 | 7/1972 | Bloch | 260/668 A |
| 3,726,941 | 4/1973 | Randall et al. | 260/683.57 |
| 4,017,224 | 8/1978 | Dwyer | 260/671 R |
| 4,650,918 | 3/1987 | Miller et al. | 585/458 |
| 4,783,567 | 11/1988 | Kocal | 585/464 |
| 4,922,053 | 5/1990 | Waguespack et al. | 585/449 |
| 5,073,653 | 12/1991 | Butler | 585/449 |
| 5,097,061 | 3/1992 | Shimizu et al. | 560/105 |
| 5,120,890 | 6/1992 | Sachtler et al. | 585/449 |
| 5,120,897 | 6/1992 | Del Rossi et al. | 585/726 |
| 5,220,095 | 6/1993 | Hommeltoft et al. | 585/720 |
| 5,245,100 | 9/1993 | Hommeltoft et al. | 585/720 |
| 5,396,017 | 3/1995 | Hommeltoft | 585/724 |
| 5,396,018 | 3/1995 | Hommeltoft | 585/724 |
| 5,414,187 | 5/1995 | King et al. | 585/730 |
| 5,491,277 | 2/1996 | Stine et al. | 585/719 |
| 5,523,503 | 6/1996 | Funk et al. | 585/446 |

FOREIGN PATENT DOCUMENTS

| | | | |
|---|---|---|---|
| 0 638 532 A1 | 2/1995 | European Pat. Off. | C07C 2/62 |
| 0 663 377 A1 | 7/1995 | European Pat. Off. | C07C 2/62 |

Primary Examiner—Glenn Caldarola
Assistant Examiner—Thuan D. Dang
Attorney, Agent, or Firm—Richard A. Kretchmer; Frank J. Stroka

[57] ABSTRACT

In a multistage process, a relatively unreactive paraffinic substrate is alkylated in a primary stage while a more reactive aromatic substrate is alkylated in a secondary stage wherein at least a portion of the effluent from the primary stage is used as a diluent in the secondary stage. The alkylation reaction in each stage is catalyzed by an acid catalyst which is adsorbed on a particulate solid support.

18 Claims, 1 Drawing Sheet

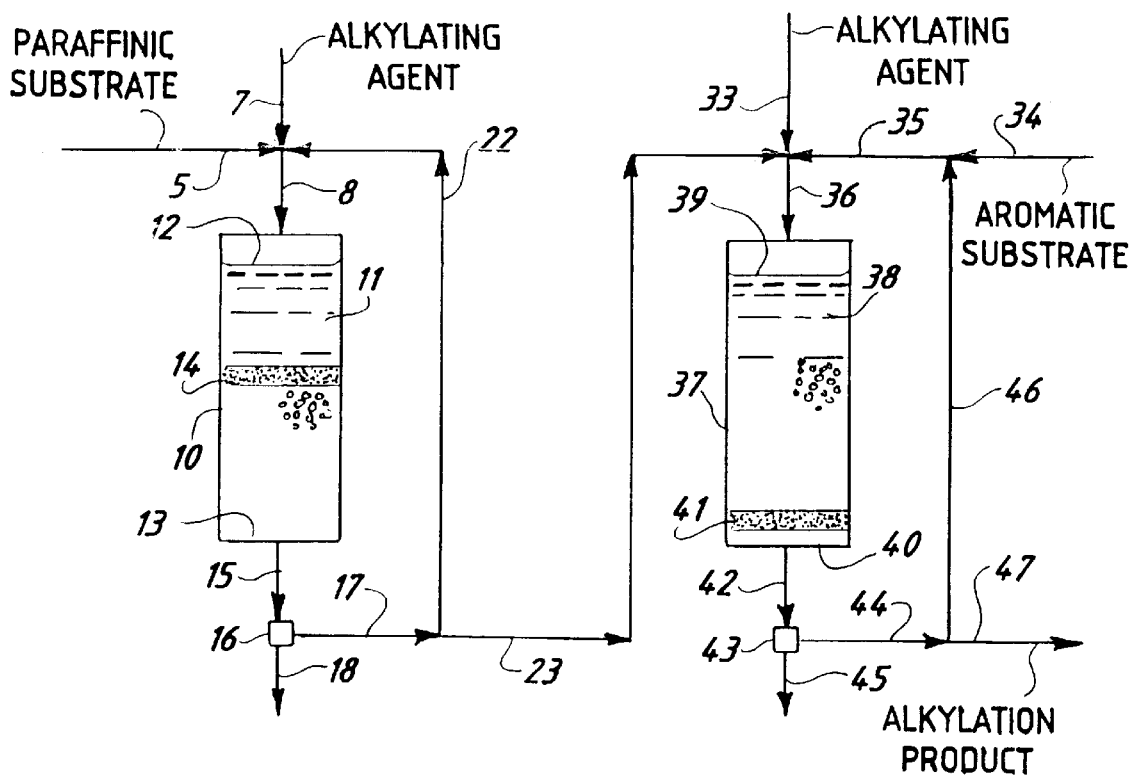

MULTISTAGE ALKYLATION PROCESS

FIELD OF THE INVENTION

This invention relates to a process for the liquid phase alkylation of an organic substrate with an olefinic alkylating agent in the presence of an acid catalyst which is adsorbed on a solid support. More particularly, it involves using a plurality of reaction zones to efficiently alkylate both paraffinic and aromatic substrates.

BACKGROUND OF THE INVENTION

The acid catalyzed addition reaction of olefins with isoparaffins is a well known process which has found extensive commercial use in the manufacture of high octane blending stocks which are used in the production of gasoline for spark-ignition engines. As typically practiced in a commercial operation, a starting material which is comprised primarily of isobutane and isopentane is alkylated with an alkylating agent which is comprised primarily of olefins which contain from 3 to 5 carbon atoms to produce a product which is comprised of branched-chain isoparaffinic hydrocarbons in the gasoline boiling range. For example, isobutane can be alkylated with 2-butene to produce 2,2,4-trimethylpentane which has a motor octane number of 100.

Concentrated sulfuric acid and anhydrous hydrofluoric acid have typically been utilized in commercial alkylation operations. However, many other acids are known to catalyze the alkylation reaction, and such materials include zeolites, aluminum chloride, and superacids, such as fluorinated sulfonic acids and sulfated zirconia.

U.S. Pat. No. 5,414,187 (King et al.) summarizes a portion of the patent literature relating to the various solid acid catalysts that have been proposed for use in promoting the acid catalyzed addition reaction of olefins with isoparaffins. In addition, King et al. disclose a catalyst for use in this reaction which comprises an organosulfonic acid having at least one covalent carbon-fluorine bond or one covalent carbon-phosphorus bond provided by a phosphono radical to increase the acidity of the organosulfonic acid and a Lewis acid complexed with at least a portion of the sulfonic acid groups. It is further disclosed that such a material can be impregnated onto a substantially inert support and employed as a supported acid catalyst.

U.S. Pat. Nos. 5,220,095 (Hommeltoft et al.) and 5,245,100 (Hommeltoft et al.) disclose that a fluorinated sulfonic acid which is adsorbed on a solid particulate polar contact material can be used as a highly efficient alkylation catalyst. These patents are directed to a process wherein a process stream comprised of a hydrocarbon substrate and an olefinic alkylating agent is passed, under alkylation conditions, through a fixed-bed alkylation reactor which contains a particulate polar contact material on which a fluorinated sulfonic acid catalyst has been adsorbed. It is disclosed that the fluorinated sulfonic acid can be adsorbed on a confined area of the polar contact material to form a movable reaction zone. When the process stream is passed through the reaction zone, the adsorbed fluorinated sulfonic acid and the reaction zone migrate on the contact material in the same direction as the flow of the process stream. With the passage of time, the fluorinated sulfonic acid and reaction zone move through the fixed-bed toward the discharge end of the alkylation reactor. The migration speed of the acid in the reactor and on the contact material is much lower than the migration speed of the hydrocarbon products and starting materials. Accordingly, a very long elution time results for the acid in comparison to that for the hydrocarbons. Suitable fluorinated sulfonic acids include fluorosulfonic acid and trifluoromethanesulfonic acid, and suitable contact materials include silica, alumina, zirconia, titania, niobium oxides, tin oxides and mixtures thereof.

The above-mentioned U.S. Pat. No. 5,220,095 (Hommeltoft et al.) teaches that when the reaction zone approaches the discharge end of the alkylation reactor, the flow direction of the process stream through the reactor can be reversed. As a consequence of this reversal of flow direction, the reaction zone also reverses its direction of movement in the contact material and moves in the same direction as the process stream. Through a periodic reversal of flow direction through the alkylation reactor, the reaction zone is moved back-and-forth from one end of the reactor to the other. Accordingly, the fluorinated sulfonic acid is never permitted to elute from the contact material and is kept within the reactor.

The above-mentioned U.S. Pat. No. 5,245,100 (Hommeltoft et al.) teaches that two reactors can be used which are connected in series. Initially, the process stream is passed sequentially through the first and the second reactors. When the reaction zone reaches the discharge end of the first reactor, the fluorinated sulfonic acid is eluted from the first reactor by the process stream and is passed into the second reactor where it is adsorbed on the contact material in the second reactor to form a new reaction zone near the inlet end of the second alkylation reactor. The flow direction of the process stream is then altered so that it is sequentially passed through the second and then the first reactor. When the fluorinated sulfonic acid is eluted from the second reactor, it is passed into the first reactor to reestablish the reaction zone in the first reactor. The flow of the process stream is then returned to its original path, and the process is repeated. Accordingly, a continuous process can be carried out wherein the reaction zone moves from one reactor to the other.

U.S. patent application Ser. No. 650,637, filed on May 20, 1996, (Mehlberg) is directed to a process for the alkylation of a hydrocarbon substrate with an olefinic alkylating agent using as a catalyst a halogenated sulfuric acid or halogenated sulfonic acid which is adsorbed on a solid particulate contact material. It is disclosed that such a process can be staged by conducting the alkylation reaction in a plurality of fixed-bed reactors which are connected in series, wherein only a portion of the olefinic alkylating agent is introduced into each fixed-bed reactor. It is further disclosed that the hydrocarbon substrate can be either: (1) straight and/or branched chain $C_2$ to $C_{10}$ paraffins; or (2) volatile aromatic compounds.

The acid catalyzed alkylation of aromatics with olefins is a well-known reaction which is of commercial importance. For example, ethylbenzene, cumene and detergent alkylate are produced by the alkylation of benzene with ethylene, propylene and $C_{10}$ to $C_{18}$ olefins, respectively. Sulfuric acid, HF, phosphoric acid, aluminum chloride, and boron fluoride are conventional catalysts which are useful for this reaction. In addition, solid acids which have a comparable acid strength can also be utilized to catalyze this process, and such materials include amorphous and crystalline aluminosilicates, clays, ion-exchange resins, mixed oxides and supported acids.

Ordinarily, aromatic hydrocarbons and paraffinic hydrocarbons can not be alkylated with an olefinic alkylating agent at the same time because aromatic hydrocarbons are much more reactive than paraffinic hydrocarbons. As a result of this significant difference in reactivity, an aromatic hydrocarbon will alkylate first. Indeed, in the event that sufficient alkylating agent is present, an aromatic (such as benzene) will typically undergo polyalkylation while a paraffin (such as isobutane) remains inert. Accordingly, the alkylation of aromatics and paraffins is usually carried out separately as separate processes with dedicated process equipment for each process.

Both current and proposed future standards for reformulated gasoline place limits on volatility and on the concentration of volatile aromatics such as benzene. Accordingly, these standards place limits on the concentration of benzene (defined as a toxic) and volatile components such as isopentane (which is a significant component of isomerate and of naphtha from a fluidized catalytic cracking unit) in gasoline. A single inexpensive process for the conversion of these materials to more desirable gasoline blending components would be highly desirable.

Low molecular weight aromatics and isoparaffins can be converted to highly desirable gasoline blending stocks by alkylation. However, there is no currently available method for the simultaneous alkylation of combinations of isobutane, isopentane, and volatile aromatics. A conventional refinery alkylation unit is typically operated to use isobutane and butenes as reactants and either sulfuric acid or HF as the catalyst to produce an alkylate that consists primarily of trimethylpentane. The addition of a volatile aromatic, such as benzene, to such a sulfuric acid alkylation unit is known to produce a significant amount of sulfonated aromatics which ruins performance of the unit. In addition, it is conventionally believed that isopentane is an unsatisfactory feedstock for such an alkylation unit because it will be much less reactive than isobutane.

BRIEF DESCRIPTION OF THE DRAWING

The drawing is a schematic representation of one embodiment of the invention wherein a series of two alkylation reactors are utilized.

SUMMARY OF THE INVENTION

This invention is directed to a process for the alkylation of paraffinic and aromatic substrates with olefinic alkylating agents which comprises:

(a) establishing a plurality of contacting zones, wherein each contacting zone is comprised of a fixed-bed of particulate solid support and wherein each contacting zone contains an acid catalyst which is adsorbed on a confined volume of the solid support;

(b) producing a first product stream of alkylation products in a primary stage by contacting an olefinic alkylating agent with a paraffinic substrate under alkylation conditions in at least one of said plurality of contacting zones;

(c) producing a process stream which is comprised of a mixture of:
  (i) at least a portion of said first product stream,
  (ii) an aromatic substrate, and
  (iii) an olefinic alkylating agent; and (d) producing a second product stream of alkylation products in a secondary stage by passing said process stream through at least one additional contacting zone of said plurality of contacting zones under alkylation conditions.

We have found that both paraffins and aromatics can be efficiently alkylated with olefins in a single alkylation unit which utilizes a plurality of reaction zones and wherein the paraffins and aromatics are separately alkylated in one or more of the reaction zones.

An object of the invention is to provide an integrated process for the alkylation of both paraffins and aromatics with olefins.

Another object of the invention is to provide a multistage alkylation process wherein paraffins are alkylated with one olefinic feedstock in a first stage while aromatics can be alkylated with another olefinic feedstock in a second stage.

Another object of the invention is to provide a method for the alkylation of both aromatics and paraffins with olefins in a multistage process over a catalyst which is comprised of an acid which is adsorbed on a particulate solid support.

Another object of the invention is to provide a multi-stage process for the conversion of: (1) benzene to gasoline blending components of reduced toxicity, and (2) isopentane to gasoline blending components of reduced volatility.

A further object of the invention is to provide an improved method for the alkylation of both isoparaffins and aromatics with olefins.

DETAILED DESCRIPTION OF THE INVENTION

We have discovered a multistage process for the alkylation of both aromatics and paraffinic hydrocarbons with an acid catalyst which is adsorbed on a particulate solid support. This process comprises the alkylation of a relatively unreactive paraffinic substrate with an olefinic alkylating agent in a primary stage, while a relatively reactive aromatic substrate is reacted with an olefinic alkylating agent in a secondary stage using at least a portion of the effluent from the primary stage as a diluent. This diluent permits an effective and convenient control over the exothermic and very facile aromatic alkylation that is carried out in the secondary stage.

The process of this invention is particularly useful for the production of a desirable high octane gasoline blending stock from undesirable volatiles such as benzene, toluene and isopentane. The alkylation of volatile aromatics with olefins which contain from 2 to 6 carbon atoms in the secondary stage of the process results in products of reduced volatility and high octane which are desirable as components of a high octane gasoline blending stock. In addition, the process is also highly satisfactory for use in carrying out the conventional alkylation of isobutane and isopentane with olefins which contain from 3 to 6 carbon atoms.

If desired, different olefinic alkylating agents can be used in the various stages of the process. For example, an olefinic alkylating agent which is comprised of at least one material selected from the group consisting of olefins which contain from 2 to 4 carbon atoms can be used in the secondary stage for the alkylation of an aromatic substrate while an olefinic alkylating agent which is comprised of at least one material selected from the group consisting of olefins which contain from 4 to 6 carbon atoms is used in the primary stage for the alkylation of a paraffinic substrate.

Suitable paraffinic substrates for use in the practice of this invention include straight and/or branched chain paraffinic hydrocarbons which contain from 3 to 20 carbon atoms. However, paraffinic hydrocarbons which contain from 3 to 10 carbon atoms are preferred, and branched chain paraffins such as isoparaffins are highly preferred. The branched chain paraffins are generally much more reactive than straight chain paraffins when treated with an olefinic alkylating agent in the presence of an acid catalyst. In addition, mixtures of such materials can be used as the paraffinic substrate in the practice of this invention. Isoparaffins such as isobutane, isopentane and isohexane are preferred paraffinic substrates for conversion to gasoline blending stock by means of alkylation with low molecular weight olefins. Isobutane, isopentane, and mixtures of isobutane with isopentane are particularly preferred as paraffinic substrates for conversion to gasoline blending stock.

Suitable aromatic substrates for use in the practice of this invention include all organic compounds of from 6 to 20 carbon atoms which contain aromatic functionality and can be alkylated by an olefin in the presence of an acid catalyst. Such materials include both aromatic compounds and substituted aromatic compounds which carry one or more substituents. Aromatic hydrocarbons and hydrocarbyl-substituted aromatic hydrocarbons which contain from 6 to 20 carbon atoms are particularly suitable. In addition, mixtures of such materials can be used as the aromatic substrate in the practice of this invention. Examples of such materials include compounds of formula I where each R is independently selected from the group consisting of hydrogen and hydrocarbyl groups. However, preferred aromatic substrates contain from 6 to 10 carbon atoms and are of formula I where each R is independently selected from the group consisting of hydrogen and alkyl of from 1 to 3 carbon atoms. Benzene and toluene are particularly preferred aromatic substrates for conversion to gasoline blending stock by alkylation with low molecular weight olefins in accordance with this invention.

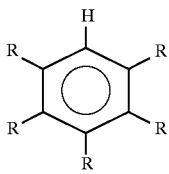
(I)

The paraffinic and aromatic substrates which are used in the practice of this invention can be obtained from any desired source. However, when gasoline blending stocks are manufactured in a petroleum refinery through the practice of this invention, crude distillation units, reformers, hydrocrackers, and isomerization units are convenient sources of the paraffinic substrate of this invention. In addition, catalytic cracking units, reformers and isomerization units are convenient sources of the aromatic substrates of this invention. It will also be appreciated that these substrates need not be pure, and can be mixed with other materials such as diluents which are substantially inert under the alkylation conditions employed in the practice of this invention. For example, an isoparaffinic substrate can contain substantial quantities of normal paraffins, which will be relatively unreactive relative to the isoparaffin in the practice of this invention.

Suitable olefinic alkylating agents for use in the practice of this invention contain from 2 to 20 carbon atoms and include cyclic olefins, substituted cyclic olefins, and olefins of formula II where $R_1$ is a hydrocarbyl group and each $R_2$ is independently selected from the group consisting of hydrogen and hydrocarbyl groups. Preferably, $R_1$ is an alkyl group and each $R_2$ is independently selected from the group consisting of hydrogen and alkyl groups. Examples of suitable cyclic olefins and substituted cyclic olefins include cyclopentene, 1-methylcyclopentene, cyclohexene, 1-methylcyclohexene, 3-methylcyclohexene, 4-methylcyclohexene, cycloheptene, cyclooctene, and 4-methylcyclooctene. Examples of suitable olefins of the type of formula II include ethylene, propylene, 2-methylpropene, 1-butene, 2-butene, 2-methyl-1-butene, 3-methyl-1-butene, 2-methyl-2-butene, 2,3-dimethyl-1-butene, 3,3-dimethyl-1-butene, 2,3-dimethyl-2-butene, 2-ethyl-1-butene, 2-ethyl-3-methyl-1-butene, 2,3,3-trimethyl-1-butene, 1-pentene, 2-pentene, 2-methyl-1-pentene, 3-methyl-1-pentene, 4-methyl-1-pentene, 2,4-dimethyl-1-pentene, 1-hexene, 2-hexene, 3-hexene, 1,3-hexadiene, 1,4-hexadiene, 1,5-hexadiene, 2,4-hexadiene, 1-heptene, 2-heptene, 3-heptene, 1-octene, 2-octene, 3-octene, and 4-octene.

(II)

Preferred olefinic alkylating agents for paraffinic substrates will contain from about 3 to about 12 carbon atoms, and preferred olefinic alkylating agents for aromatic substrates will contain from 2 to about 12 carbon atoms. Highly preferred alkylating agents will contain from about 2 or 3 to about 6 carbon atoms. In addition, mixtures of olefins can be used as an olefinic alkylating agent in the practice of this invention. For example, a paraffinic substrate can be alkylated with an olefinic alkylating agent which is comprised of a mixture of olefins which are selected from the group consisting of olefins which contain from 3 to 6 carbon atoms. Similarly, an aromatic substrate can be alkylated with an olefinic alkylating agent which is comprised of at least one material which is selected from the group consisting of olefins which contain from 2 to 6 carbon atoms. Finally, it will be understood that the olefinic alkylating agents can contain diluents which will be relatively inert under the alkylation conditions which are employed in the practice of this invention.

The olefinic alkylating agents which are used in the practice of this invention can be obtained from any desired source. However, when gasoline blending stocks are manufactured in a petroleum refinery through the practice of this invention, catalytic cracking units and coking units are convenient sources of olefins which can be used as the olefinic alkylating agent of this invention. Such olefinic process streams from a catalytic cracking unit or a coking unit will also typically contain significant amounts of isobutane which can be used as a paraffinic substrate in the practice of this invention.

The acid catalyst employed in the practice of the present invention can be any acidic material which: (1) can catalyze the reaction of the selected olefinic alkylating agent with the selected paraffinic or aromatic substrate; and (2) can be adsorbed on the particulate solid support of this invention. Preferably, the acid catalyst is one which can be adsorbed on a confined volume of a fixed-bed of the particulate solid support and undergoes a slow migration or elution through the fixed-bed as a process stream of olefinic alkylating agent and paraffinic or aromatic substrate is passed through the fixed-bed under alkylation conditions. In addition, the acid catalyst will preferably be a liquid under ambient conditions to simplify transfer, separation and recovery of the catalyst and also the regeneration or purification of the recovered catalyst. Suitable acid catalysts include fluorinated sulfonic acids such as fluorosulfonic acid and sulfonic acids of the formula $R(SO_3H)_x$ where R is an organo radical having at least one covalent carbon-fluorine bond and x is an integer from 1 to 3. Fluorosulfonic acid and fluorinated alkane sulfonic acids such as trifluoromethanesulfonic acid are particularly useful in the practice of this invention.

The particulate solid which is used as a fixed-bed support for the acid catalyst of this invention can be any particulate solid which can adsorb the catalyst and does not react or disintegrate under the conditions of use. Suitable materials include polar solids which have sufficient adsorption capacity for the acid catalyst relative to that for the process stream of reactants and products so that the acid catalyst migrates or elutes through the fixed-bed very slowly in comparison to the components of the process stream. Preferred materials for use as the particulate solid support include, but are not limited to, silica, alumina, zirconia, titania, the oxides of tin and the lanthanides, and mixtures thereof.

Desirably, the particulate solid support for the acid catalyst will be used in a physical form, such as pellets, beads or rods, which will permit a rapid and effective contacting with the paraffinic or aromatic substrate and the olefinic alkylating agent without creating substantial amounts of backpressure. Although the invention is not to be so limited, it is preferred that the solid support be in particulate form wherein the largest dimension of the particles has an average value which is in the range from about 0.01 mm to about 2 cm. For example, substantially spherical beads of catalyst can be used which have an average diameter from about 0.1 mm to about 2 cm. Alternatively, the catalyst can be used in the form of rods which have a diameter in the range from about 0.1 mm to about 1 cm and a length in the range from about 0.2 mm to about 2 cm.

In the practice of this invention, process conditions are maintained in each reactor or reaction zone which are effective to permit the desired alkylation reaction to take place between the olefinic alkylating agent and the paraffinic or aromatic substrate. Typically, the alkylation reaction will be carried out at a temperature in the range from about −50° to about 100° C. and preferably in the range from about −15° to about 50° C. A pressure in the range from about 1 to about 100 atmospheres will typically be used, with the precise value depending on the composition of the process stream and the reaction temperature selected. When isobutane and isopentane are alkylated with olefins which contain from 3 to 5 carbon atoms at temperatures above about −10° C., it will be necessary to use superatmospheric pressures if the reactants are to be maintained substantially in the liquid state. In general, it is preferable to use pressures sufficient to maintain the reactants in the liquid phase, although vapor phase operation can be carried out if desired.

The number of alkylation reactors employed in the practice of this invention can vary from 2 to as many as 20 or more. In the primary stage of the process, from 1 to as many as 20 or more reactors are utilized in series for the alkylation of the paraffinic substrate with the olefinic alkylating agent. With reference to this primary stage, preferably from 1 to 10 reactors are used. With further reference to the primary stage of the process and where x is the number of reactors used in the primary stage, the fraction of the total amount of primary stage olefinic alkylating agent that is introduced into each alkylation reactor in the primary stage series is $1/x \pm$ up to 0.3, preferably $1/x \pm$ up to 0.1, and more preferably $1/x$.

The use of a plurality of alkylation reactors in the primary stage of the process is particularly desirable because it permits the use of low concentrations of olefinic alkylating agent and large mole ratios of paraffinic substrate to olefinic alkylating agent. This is important because such conditions serve to enhance the desired formation of monoalkylation products and minimize the formation of undesired products such as polyalkylation products and polymers resulting from polymerization of the olefinic alkylating agent. In addition, the use of a plurality of alkylation reactors makes it easier to manage the heat which is produced by the exothermic alkylation reaction since the reaction is carried in a plurality of reaction zones rather than in a single reaction zone. The use of a plurality of alkylation reactors for the alkylation of a hydrocarbon substrate with an olefin in the presence of a halogenated sulfuric acid or halogenated sulfonic acid which is adsorbed on a solid particulate contact material is disclosed by U.S. patent application Ser. No. 650,637, filed on May 20, 1996. This patent application is hereby incorporated by reference.

If desired, a plurality of alkylation reactors can also be used in the secondary stage of this invention. In the secondary stage, a plurality of reactors can useful for heat management since the heat from the exothermic alkylation of the aromatic substrate will be distributed over a plurality of reaction zones. In addition, such a plurality of reactors in the secondary stage can be used to easily maintain a large mole ratio of aromatic substrate to olefinic alkylating agent. Such a large mole ratio will serve to enhance the formation of monoalkylation products and minimize the formation of polyalkylation products and polymers resulting from polymerization of the olefinic alkylating agent. However, the formation of undesired products in the secondary stage of this invention will usually be less of a problem than in the primary stage because the aromatic substrate will be much more reactive than the paraffinic substrate. As a consequence, relative to the primary stage, higher concentrations of olefinic alkylating agent can usually be used in the secondary stage without significant increase in polymer formation from polymerization of the alkylating agent. The principal side-reaction that must be managed in the secondary stage is polyalkylation of the substrate. It will also be appreciated that polyalkylation of the aromatic substrate may be acceptable or even desirable. Such a situation may occur, for example, when a volatile aromatic such as benzene is alkylated with a low molecular weight olefin such as ethylene or propylene.

The fresh feed to any particular alkylation reactor employed in the method of the present invention is the amount of fresh alkylating agent and substrate which is introduced into that reactor. Accordingly, the amount of any substrate that is recycled to the reactor is not included in the calculation of the amount of fresh feed. When isobutane and isopentane are alkylated with olefins which contain from 3 to 5 carbon atoms in the first stage of the subject invention, a portion of the paraffinic substrate can be recycled as a refrigerant and/or as a diluent. The weight ratio of the paraffinic substrate to the olefinic alkylating agent in the fresh feed for a reactor (conventionally referred to as the "external weight ratio") will typically be in the range from about 2 to about 100, preferably in the range from about 4 to about 20, and more preferably in the range from about 7 to about 12. The weight ratio of the aromatic substrate to the olefinic alkylating agent in the fresh feed for a reactor will typically be in the range from about 0.25 to about 100, preferably in the range from about 0.5 to about 20, and more preferably in the range from about 0.5 to about 10.

The total feed to any specific alkylation reactor employed in the practice of this invention is the combination of the above-defined fresh feed and the total amount of any substrate and olefinic alkylating agent recycled to the reactor. The weight ratio of the paraffinic substrate to the olefinic alkylating agent in the total feed for a reactor will typically be in the range from about 4 to about 1000, preferably from about 10 to about 100, and more preferably from about 10 to about 30. The weight ratio of the aromatic substrate to the olefinic alkylating agent in the total feed for a reactor will typically be in the range from about 0.25 to about 100, preferably in the range from about 0.5 to about 20, and more preferably in the range from about 0.5 to about 10.

A number of alternatives are available in the practice of the present invention for handling the product stream that is withdrawn from a specific reactor and comprises alkylation products and unreacted substrate. These alternatives include but are not limited to the following: (1) the entire product stream can be transferred to the next reactor in the series; (2) a portion of the alkylation product can be removed from the product stream with the remainder being transferred to the next reactor in the series; (3) a lower boiling inert such as propane can be removed from the product stream with the remainder being transferred to the next reactor in the series; (4) a portion of the alkylation product and a lower boiling inert are both removed from the product stream with the remainder being transferred to the next reactor in the series; and (5) a portion of the product stream is recycled to the reactor from which it was withdrawn while a second portion is transferred to the next reactor in the series, optionally after at least a portion of the alkylation product is removed from such second portion.

While this invention is susceptible of embodiment in many forms, a specific embodiment is shown schematically in the DRAWING, with the understanding that the present disclosure is not intended to limit the invention to the embodiment illustrated.

With reference to the DRAWING, a fresh supply of a paraffinic substrate is introduced through line 5 and is combined with an olefinic alkylating agent which is introduced through line 7. The resulting mixture of paraffinic substrate and olefinic alkylating agent is passed through line 8 and is introduced into alkylation reactor 10 which contains a fixed-bed 11 of a suitable particulate solid support.

A suitable acid catalyst, such as trifluoromethanesulfonic acid, is initially adsorbed on a confined volume of the particulate solid support near the input end 12 of fixed-bed 11. The acid catalyst is adsorbed strongly on the solid support and forms a narrow reaction zone which slowly moves toward the output end 13 of fixed-bed 11 during the process. This reaction zone 14 is shown near the middle of the fixed-bed 11. Within reaction zone 14, the mixture of paraffinic substrate and olefinic alkylating agent undergoes reaction to yield a product stream which is comprised of alkylation products together with any unreacted starting materials and inert diluents if any are used. However, because of the high rate of the alkylation reaction under typical alkylation conditions and the high ratio of paraffinic substrate to olefinic alkylating agent which is ordinarily used, there will ordinarily be very little unreacted alkylating agent in the resulting product stream. This product stream is discharged from reactor 10 through line 15.

During the operation of reactor 10, the acid catalyst and reaction zone 14 migrate through fixed-bed 11 toward its output end 13 as a consequence of interaction of the acid catalyst with the process stream flowing through reactor 10. The migration speed of the acid catalyst (and hence of reaction zone 14) through fixed-bed 11 of particulate solid support is much slower than the flow of the process stream through fixed-bed 11. Accordingly, large volumes of the process stream can be passed through reactor 10 before the acid catalyst (and reaction zone 14) reaches the output end 13 of fixed-bed 11.

When reaction zone 14 reaches the output end 13 of fixed-bed 11, the acid catalyst passes through line 15 and is separated from the process stream in separator 16. Any conventional separation device or system can be employed as separator 16. For example, a liquid-liquid decanter or cyclone can be used to separate a liquid acid catalyst from the process stream. The resulting substantially catalyst-free process stream then passes through line 17, and the separated acid catalyst is removed through line 18. The acid catalyst which is recovered through line 18 can be reused, optionally after purification or regeneration.

If desired, the process stream in line 17 can be split into a recycle stream, which is returned to reactor 10 through lines 22 and 8, and an effluent stream which is passed through line 23. In addition, the recycle stream can be cooled by any conventional technique, such as evaporative cooling or by refrigeration, to help manage the heat which is produced in reactor 10 by the exothermic alkylation reaction.

When reaction zone 14 reaches or nears the output end 13 of fixed-bed 11, another batch of acid catalyst is introduced into a confined volume of the particulate solid support near the input end 12 of fixed-bed 11. If desired, recovered acid catalyst from line 18 can be used for this purpose.

The effluent stream from reactor 10 is passed through line 23 and is combined with an olefinic alkylating agent which is introduced through line 33 and an aromatic substrate which is introduced through lines 34 and 35. The olefinic alkylating agent introduced through line 33 can either be the same or different from the alkylating agent which is introduced through line 7. The resulting mixture of effluent from reactor 10, olefinic alkylating agent, and aromatic substrate is passed through line 36 and is introduced into alkylation reactor 37, which contains a fixed-bed 38 of a suitable particulate solid support.

A suitable acid catalyst, such as trifluoromethanesulfonic acid, is initially deposited within a confined volume of the particulate solid support near the input end 39 of fixed-bed 38. If desired, a different acid catalyst can be used from the one used in fixed-bed 11. However, it will generally be convenient to use the same acid catalyst in both fixed-beds 11 and 38. The acid catalyst is adsorbed strongly on the solid support and forms a narrow reaction zone which slowly moves toward the output end 40 of fixed-bed 38 during the process. This reaction zone 41 is shown near the end of the fixed-bed 38. Within reaction zone 41, the aromatic substrate is alkylated by the olefinic alkylating agent to yield a product stream which is comprised of alkylated aromatic substrate.

During the operation of reactor 37, the acid catalyst and reaction zone 41 migrate through fixed-bed 38 toward its output end 40 as a consequence of interaction of the acid catalyst with the process stream flowing through reactor 37. The migration speed of the acid catalyst (and hence of reaction zone 41) through fixed-bed 38 of particulate solid support is much slower than the flow of the process stream through fixed-bed 38. Accordingly, large volumes of the process stream can be passed through reactor 37 before the acid catalyst (and reaction zone 41) reaches the output end 40 of fixed-bed 38.

When reaction zone 41 reaches the output end of fixed-bed 38, the acid catalyst passes through line 42 and is separated from the process stream in separator 43. Any conventional separation device or system can be employed as separator 43. For example, a liquid-liquid decanter or liquid cyclone can be used to separate a liquid acid catalyst from the process stream. The resulting substantially catalyst-free process stream then passes through line 44, and the separated acid catalyst is removed through line 45. The acid catalyst which is recovered through line 45 can be reused, optionally after purification or regeneration.

When reaction zone 41 reaches or nears the output end 40 of fixed-bed 38, another batch of acid catalyst is introduced into a confined volume of the particulate solid support near the input end 39 of fixed-bed 38. If desired, recovered acid catalyst from line 45 can be used for this purpose.

If desired, the process stream in line 44 can be split into a recycle stream, which is returned to reactor 37 through lines 46, 35 and 36, and a product stream which is passed through line 47. In addition, the recycle stream can be cooled by any conventional technique, such as evaporative cooling or by refrigeration, to help manage the heat which is produced in reactor 37 by the exothermic alkylation reaction.

Product from the alkylation process, which comprises alkylated paraffinic substrate from reactor 10 and alkylated aromatic substrate from reactor 37 is recovered from line 47.

EXAMPLE I

The alkylation of isobutane with 1-butene over trifluoromethanesulfonic acid was carried out in a 0.95 cm internal diameter tubular reactor which was constructed of stainless steel and packed with 15 g of silica gel. The packed bed had a length of 30.5 cm, and a 0.16 cm outside diameter tubular thermowell was concentrically located across the entire length of the silica gel bed. A 9.7 g portion of trifluoromethanesulfonic acid was initially adsorbed on the silica gel at the inlet end of the silica gel bed to create a reaction zone. Since the alkylation reaction is exothermic and takes place only in the presence of the trifluoromethanesulfonic acid, the location and temperature of the reaction zone could be monitored during the experiment by manually moving a Type K thermocouple within the thermowell. A mixture of isobutane and 1-butene were passed through the silica gel bed and reaction zone at a flow rate of 266 cm$^3$/hr and 7.7 cm$^3$/hr respectively. With an inlet temperature of 4° C. for the isobutane and 1-butene reactants, the temperature in the reaction zone increased by a maximum of about 17° to 20° C., and the reaction zone moved by about 0.28 cm/min in the same direction as the flow of reactants through the silica gel bed. The principal products were trimethylpentanes, and the product composition as a function of carbon number is set forth in Table I.

TABLE I

Product Distribution from Alkylation of Isobutane with 1-Butene

| Carbon Number of Products | Wt. % of Total Products |
|---|---|
| C5 | 1 |
| C6 | 1 |
| C7 | 2 |
| C8 | 92 |
| C9 | 1 |
| C10 | 2 |
| C11 | 2 |
| C12 | 1 |

EXAMPLE II

A mixture of isopentane and isobutane was alkylated with 1-butene in the manner described in Example I using a 7.8 g portion of trifluoromethanesulfonic acid. A mixture of isopentane, isobutane and 1-butene was passed through the silica gel bed and reaction zone at flow rates of 33 cm$^3$/hr, 200 cm$^3$/hr and 9.3 cm$^3$/hr, respectively. With an inlet temperature of 18° C. for the mixture of reactants, the temperature in the reaction zone increased by a maximum of about 25° C., and the reaction zone moved by about 0.30 cm/min in the same direction as the flow of reactants through the silica gel bed. The principal products were trimethylpentanes and trimethylhexanes, and the product composition as a function of carbon number is set forth in Table II. The mole ratio of C$_8$ to C$_9$ products of 6.5 was nearly the same as the 6.1 mole ratio of isobutane to isopentane in the mixture of reactants. Accordingly, isopentane and isobutane have substantially the same reactivity toward 1-butene in the presence of trifluoromethanesulfonic acid which is adsorbed on silica gel.

TABLE II

Product Distribution from Alkylation of a Mixture of Isopentane and Isobutane with 1-Butene

| Carbon Number of Products | Wt. % of Total Products |
|---|---|
| C6 | 5 |
| C7 | 5 |
| C8 | 70 |
| C9 | 12 |
| C10 | 4 |
| C11 | 4 |
| C12 | 1 |

EXAMPLE III

A mixture of isobutane, benzene and toluene was alkylated with propylene in the manner described in Example I using a 4.4 g portion of trifluoromethanesulfonic acid. A mixture of isobutane, benzene, toluene and propylene was passed through the silica gel bed and reaction zone at flow rates of 200 cm$^3$/hr, 20.3 cm$^3$/hr, 6.7 cm$^3$/hr and 10 cm$^3$/hr, respectively. With an inlet temperature of 16° C. for the mixture of reactants, the temperature in the reaction zone increased by a maximum of about 33° to 36° C., and the reaction zone moved by about 0.25 cm/min in the same direction as the flow of reactants through the silica gel bed. The conversion of benzene and toluene to alkylation products was 30% and 29%, respectively. The products consisted of 55 wt % cumene (isopropylbenzene), 22 wt % cymene (isopropyltoluene), and 23 wt % di(isopropyl)benzene. Isobutane alkylation did not occur.

We claim:

1. A process for the alkylation of paraffinic and aromatic substrates with olefinic alkylating agents which comprises:
   (a) establishing a plurality of contacting zones, wherein each contacting zone is comprised of a fixed-bed of particulate solid support and wherein each contacting zone contains an acid catalyst which is adsorbed on a confined volume of the solid support;
   (b) producing a first product stream of alkylation products in a primary stage by reacting a primary stage olefinic alkylating agent with a paraffinic substrate under alkylation conditions in at least one of said plurality of contacting zones;
   (c) producing a process stream by combining at least a portion of said first product stream with both an aromatic substrate and a secondary stage olefinic alkylating agent, wherein said primary and secondary stage olefinic alkylating agents are either the same or different; and
   (d) reacting said aromatic substrate with said secondary stage olefinic alkylating agent in a secondary stage by passing said process stream through at least one additional contacting zone of said plurality of contacting zones under alkylation conditions.

2. The process of claim 1 wherein at least two contacting zones are used in said primary stage for production of the first product stream and wherein:

(a) the primary stage contacting zones are connected in series;

(b) a feedstock which is comprised of the paraffinic substrate and a portion of the primary stage olefinic alkylating agent is passed through the first of said series of primary stage contacting zones;

(c) an intermediate feedstock is prepared for each subsequent member of the series of primary stage contacting zones by combining a portion of the primary stage olefinic alkylating agent with at least a portion of the effluent from the preceding member of the series, wherein said effluent comprises unreacted paraffinic substrate; and (d) each intermediate feedstock is passed through the subsequent member of said series of primary stage contacting zones.

3. The process of claim 2 wherein the number of contacting zones in said primary stage is from 2 to 20.

4. The process of claim 1 wherein at least two contacting zones are used in said primary stage for production of the first product stream and wherein:

(a) the primary stage contacting zones are connected in series; and (b) a feedstock which is comprised of a portion of the paraffinic substrate and a portion of the primary stage olefinic alkylating agent is passed through the first of said series of primary stage contacting zones; and (c) a portion of the primary stage olefinic alkylating agent and a portion of the paraffinic substrate is passed through each subsequent member of said series of primary stage contacting zones in combination with at least a portion of the effluent from the preceding member of the series of primary stage contacting zones.

5. The process of claim 1 wherein the primary stage olefinic alkylating agent is comprised of at least one material which is selected from the group consisting of olefins which contain from 3 to 6 carbon atoms.

6. The process of claim 1 wherein the primary stage olefinic alkylating agent is comprised of a mixture of olefins which are selected from the group consisting of olefins which contain from 3 to 6 carbon atoms.

7. The process of claim 1 wherein the paraffinic substrate is comprised of at least one material which is selected from the group consisting of isobutane and isopentane.

8. The process of claim 1 wherein the paraffinic substrate is comprised of a mixture of isobutane and isopentane.

9. The process of claim 1 wherein the secondary stage olefinic alkylating agent is comprised of at least one material which is selected from the group consisting of olefins which contain from 2 to 6 carbon atoms.

10. The process of claim 9 wherein the secondary stage olefinic alkylating agent is comprised of propylene.

11. The process of claim 1 wherein the secondary stage olefinic alkylating agent is comprised of a mixture of olefins which are selected from the group consisting of olefins which contain from 2 to 6 carbon atoms.

12. The process of claim 1 wherein the aromatic substrate is comprised of at least one material which is selected from the group consisting of benzene and toluene.

13. The process of claim 1 wherein the acid catalyst is a fluorinated sulfonic acid.

14. The process of claim 13 wherein the acid catalyst is selected from the group consisting of fluorosulfonic acid and trifluoromethanesulfonic acid.

15. The process of claim 1 wherein said primary stage and secondary stage olefinic alkylating agents are the same.

16. The process of claim 1 wherein said primary stage and secondary stage olefinic alkylating agents are different.

17. The process of claim 16 wherein the primary stage olefinic alkylating agent is comprised of at least one material which is selected from the group consisting of olefins which contain from 4 to 6 carbon atoms and the secondary stage olefinic alkylating agent is comprised of at least one material which is selected from the group consisting of olefins which contain from 2 to 4 carbon atoms.

18. The process of claim 1 wherein the acid catalyst used in said primary stage is different from the acid catalyst which is used in said secondary stage.

* * * * *